United States Patent [19] [11] 3,934,009
Gey et al. [45] Jan. 20, 1976

[54] AGENTS FOR LOWERING THE LIPID LEVEL IN PLASMA

[75] Inventors: Karl Friedrich Gey, Reinach; Joseph Kiss, Arlesheim; Hans Lengsfeld, Reinach; Willy Schuep, Birsfelden; Pierre-Charles Wyss, Muttenz, all of Switzerland

[73] Assignee: Hoffmann-La Roche Inc., Nutley, N.J.

[22] Filed: Jan. 9, 1975

[21] Appl. No.: 539,662

[30] Foreign Application Priority Data
Jan. 25, 1974  Switzerland.......................... 1038/74

[52] U.S. Cl............................. 424/180; 260/211 R

[51] Int. Cl.² ........................................ A61K 31/70
[58] Field of Search .................................... 424/180

[56] References Cited
UNITED STATES PATENTS
3,851,057  11/1974  Kuzuya et al. ...................... 424/180

Primary Examiner—Lewis Gotts
Assistant Examiner—Cary Owens
Attorney, Agent, or Firm—Samuel L. Welt; Jon S. Saxe; George M. Gould

[57] ABSTRACT

N-nicotinoylglucosamine as a lipid level lowering agent in plasma.

7 Claims, No Drawings

AGENTS FOR LOWERING THE LIPID LEVEL IN PLASMA

PRIOR ART

N-Nicotinoylglucosamine is a known compound which can be present in the form of N-nicotinoyl-L-glucosamine or N-nicotinoyl-D-glucosamine. The activity of N-nicotinoyl-D-glucosamine against tubercule bacilli and amoebae as well as its blocking action on the growth of tumors are known from U.S. Pat. No. 3,014,027.

Japanese Pat. No. 4734366 describes 2-acetamido-2-deoxy-D-glucopyranose-6-nicotinate as a blood vessel dilator.

Japanese Pat. No. 4800472 describes polysaccharide nicotinate as a blood vessel dilator.

German Pat. No. 1,942,457 and 1,966,666 describe nicotinic acid esters of polyfructoses as having serum cholesterol level lowering activity.

DESCRIPTION OF THE INVENTION

The present invention is concerned with agents for lowering the lipid level in plasma. The invention is also concerned with a process for the preparation of said agents.

The present invention is based on the finding that N-nicotinoylglucosamine possesses a plasma-lipid lowering activity.

Accordingly, the agents for lowering the lipid level in plasma provided by the present invention contain N-nicotinoylglucosamine as the essential active ingredient.

Beta-pyridylcarbinol and nicotinic acid are compounds which have been clinically proved for lowering plasma lipids for a number of years. A substantial disadvantage of these compounds is, however, their rapid resorption from the intestine and the resulting steep increase of the plasma nicotinic acid level. This leads on the one hand frequently to undesired side-effects (skin reddening and burning, especially in the face) and on the other hand, because of the rapid metabolism of the nicotinic acid, to a quick decrease of the plasma level and, concomitantly, an end of the activity. Thus, repeated efforts have been made and are being made to provide derivatives of nicotinic acid which are cleaved more slowly in the body in order that the nicotinic acid liberated cannot be resorbed so rapidly that these side-effects occur.

Examples of such derivatives of nicotinic acid which have been proposed are nicofuranose (tetranicotinyl-fructose) and niceritrol (pentaerythritol tetranicotinate). These derivatives do, in fact, provide a lengthening of the resorption time. However, there has been a desire to find a derivative in which the lengthening of the resorption time appears even more pronounced.

The desired objective has been achieved by the provision of the agents in accordance with the present invention.

As compared with beta-pyridylcarbinol, nicotinic acid, niceritrol and nicofuranose which, when administered to rats in an amount of 1 mmol/kg (based on the respective pyridyl groups), lead to an excessive and short-lived maximum of the nicotinic acid concentration in the plasma, N-nicotinoyl-glucosamine leads to a distinctly more moderate and longer-lasting increase of the nicotinic acid concentration in the plasma. Accordingly, in the case of N-nicotinoylglucosamine administration, the reduction of free fatty acids, cholesterol and triglycerides in plasma also lasts several hours longer than in the case of administration of beta-pyridylcarbinol, nicotinic acid, niceritrol or nicofuranose. The phenomenon of the reactive overshoot ("rebound" phenomenon) of the free fatty acids, triglycerides and cholesterol above the starting values after a temporary lowering, is completely absent in the case of administration of N-nicotinoylglucosamine or is noticeably weaker than in the case of administration of beta-pyridylcarbinol, nicotinic acid, niceritrol or nicofuranose. By "reactive overshoot", there is to be understood the increase, after a temporary lowering, of the lipids above the starting value present before the administration of the lipid-lowering agent.

In the case of a single oral administration of 1–2 g. of N-nicotinoylglucosamine to healthy volunteers no "flush" (unpleasant reddening and sensation of heat on the face) occurs while, in the case of administration of even 0.5–1 g. of nicotinic acid, a considerable flush can be observed.

The amount of N-nicotinoylglucosamine administered to achieve a lowering of the lipid level in plasma is in the range of from about 5 to 30 mg/kg., preferably about 10 to 20 mg/kg., daily.

The foregoing dosages are, however, only given by way of example and can be increased or decreased depending on the particular circumstances or administration forms under consideration.

The agents for lowering the lipid level in plasma can be prepared by adding N-nicotinoylglucosamine as the essential active ingredient to compatible carrier material. Such carrier material can be inert, solid or liquid carriers common in pharmaceutical preparations and suitable for therapeutic administration.

Examples of suitable carrier materials are water, gelatin, gum arabic, lactose, starch, magnesium stearate, talc, vegetable oils, polyalkyleneglycols, petroleum jelly, etc. The pharmaceutical preparations can be made up in a solid form (e.g., as tablets, dragees, suppositories or capsules) or in a liquid form (e.g., as solutions, suspensions or emulsions). The pharmaceutical preparations may be sterilized and/or may contain adjuvants such as preservatives, stabilizers, wetting agents, emulsifiers, salts for varying the osmotic pressure or buffers. They can also contain other therapeutically valuable substances.

A preferred dosage form is tablets containing about 200 to 2000 mg. of active ingredient.

The preferred form of active ingredient is N-nicotinoyl-D-glucosamine.

Toxicity tests carried out on the mouse and rat using N-nicotinoyl-D-glucosamine gave the following results:

| | | Lethal doses in mg/kg. p.o. | | |
|---|---|---|---|---|
| | | 24 hrs. after 1st. adminis. | 24 hrs. after 5th adminis. | 10 days after 5th adminis. |
| In the mouse | $DL_{10}$ | 5087 | 1002 | 1002 |
| | $DL_{50}$ | 8000±1288 | 3752±1121 | 3752±1121 |
| | $DL_{90}$ | over 8000 | over 8000 | over 8000 |
| In the rat | $DL_{10}$ | over 8000 | over 8000 | over 8000 |
| | $DL_{50}$ | over 8000 | over 8000 | over 8000 |
| | $DL_{90}$ | over 8000 | over 8000 | over 8000 |

The following example illustrates the present invention:

EXAMPLE

Tablets of the following composition are prepared:

| | |
|---|---|
| N-nicotinoyl-D-glucosamine | 500 mg. |
| Citric acid | 5 mg. |
| Maize starch | 60 mg. |
| Microcrystalline cellulose | 120 mg. |
| Carboxymethylcellulose | 10 mg. |
| Magnesium stearate | 5 mg. |
| Total weight | 700 mg. |

These tablets can be prepared by mixing the N-nicotinoyl-D-glucos-amine and the citric acid with a portion of the maize starch and the micro-crystalline cellulose, granulating the mixture with an aqueous, alcoholic slurry of carboxymethylcellulose, drying the granulated product, adding the remaining adjuvants and pressing the product obtained to tablets.

We claim:

1. A composition useful for lowering the lipid level in plasma comprising N-nicotinoylglucosamine and a pharmaceutical carrier material.

2. The composition of claim 1 which contains 200 to 2000 mg. of N-nicotinoylglucosamine per dosage unit.

3. The composition of claim 1 which contains N-nicotinoyl-D-glucosamine.

4. A method for lowering the lipid level in plasma which method comprises administering to a subject a lipid level lowering amount of N-nicotinoylglucosamine.

5. The method of claim 4 wherein N-nicotinoyl-D-glucosamine is used.

6. The method of claim 4 wherein a total of from about 5 to 30 mg/kg of N-nicotinoylglucosamine is administered daily.

7. The method of claim 4 wherein said N-nicotinoylglucosamine is administered in oral dosage form.

* * * * *